(12) United States Patent
Yaniv et al.

(10) Patent No.: US 8,512,641 B2
(45) Date of Patent: Aug. 20, 2013

(54) MODULATION OF STEP FUNCTION PHENOMENA BY VARYING NANOPARTICLE SIZE

(75) Inventors: Zvi Yaniv, Austin, TX (US); Donald R. Schropp, Jr., Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 1742 days.

(21) Appl. No.: 11/696,617

(22) Filed: Apr. 4, 2007

(65) Prior Publication Data

US 2007/0238209 A1    Oct. 11, 2007

Related U.S. Application Data

(60) Provisional application No. 60/791,130, filed on Apr. 11, 2006.

(51) Int. Cl.
G01N 27/04 (2006.01)

(52) U.S. Cl.
USPC ............................... 422/88; 422/98; 977/957

(58) Field of Classification Search
USPC ................. 422/50, 83, 88, 98; 977/902, 932, 977/953, 957
See application file for complete search history.

(56) References Cited

U.S. PATENT DOCUMENTS

| | | | |
|---|---|---|---|
| 4,240,879 A | 12/1980 | Dobson | |
| 4,324,760 A | 4/1982 | Harris | |
| 5,670,115 A | 9/1997 | Cheng et al. | |
| 5,886,614 A | 3/1999 | Cheng et al. | |
| 6,103,540 A | 8/2000 | Russell et al. | |
| 6,120,835 A | 9/2000 | Perdieu | |
| 6,359,288 B1 | 3/2002 | Ying et al. | |
| 6,450,007 B1 | 9/2002 | O'Connor | |
| 6,465,132 B1 | 10/2002 | Jin | |
| 6,525,461 B1 | 2/2003 | Iwasaki et al. | |
| 6,535,658 B1 | 3/2003 | Mendoza et al. | |
| 6,673,644 B2 | 1/2004 | Gole et al. | |
| 6,737,286 B2 | 5/2004 | Tao et al. | |
| 6,770,353 B1 | 8/2004 | Marilovich et al. | |
| 6,788,453 B2 | 9/2004 | Banin et al. | |
| 6,849,911 B2 | 2/2005 | Monty et al. | |
| 6,882,051 B2 | 4/2005 | Majumdar et al. | |
| 2002/0079999 A1 | 6/2002 | Jin | |
| 2002/0117659 A1 | 8/2002 | Lieber et al. | |
| 2002/0132361 A1 | 10/2002 | Jin | |
| 2003/0079999 A1 | 5/2003 | Pender et al. | |
| 2003/0135971 A1 | 7/2003 | Liberman et al. | |
| 2003/0139003 A1 | 7/2003 | Gole et al. | |
| 2003/0189202 A1 | 10/2003 | Li et al. | |
| 2004/0023428 A1 | 2/2004 | Gole et al. | |
| 2004/0067646 A1 | 4/2004 | Tao et al. | |
| 2004/0070006 A1 | 4/2004 | Monty et al. | |
| 2004/0071951 A1 | 4/2004 | Jin | |
| 2004/0104129 A1 | 6/2004 | Gu et al. | |
| 2004/0118698 A1 | 6/2004 | Lu et al. | |
| 2005/0005675 A1 * | 1/2005 | Monty et al. | ................... 73/23.2 |
| 2005/0072213 A1 | 4/2005 | Besnard et al. | |
| 2005/0155858 A1 * | 7/2005 | Monty et al. | .................. 204/424 |

OTHER PUBLICATIONS

F. Favier et al., Hydrogen Sensors and Switches from Electrodeposited Palladium Mesowire Arrays, 293 Science 2227-2231 (2001).*

E.C. Walter et al., Palladium Mesowire Arrays for Fast Hydrogen Sensors and Hydrogen-Actuated Switches, 74 Anal. Chem. 1546-1553 (2002).*

Favier et al., "Hydrogen Sensors and Switches from Electrodeposited Palladium Mesowire Arrays", Science, vol. 293, pp. 2227-2231 (2001).

Jayaraman et al., "Synthesis and hydrogen permeation properties of ultrathin palladium-silver alloy membranes", Journal of Membrane Science, pp. 251-262 (1995).

Keuler et al., "Characterization of electrodes plated palladium-silver alloy membranes", Thin Solid Films, vol. 347, pp. 91-98 (1999).

Oh et al., "H NMR Study of Hydrogen in Palladium Nanocrystals", Journal of the Korean Physical Society, vol. 43(6), pp. 958-962 (2003).

Suleiman et al., "The effect of the cluster structure in the phase transition during hydrogen absorption", Annual Reports of Deutsches Elektronen-Synchronton (DESY) 2002.

Suleiman et al., "Pd-H clusters: non-bulk like behavior", Annual reports of Deutsches Elektronen0Synchronton (DESY) (2003).

Tong, H.D., et al., "A Hydrogen Separation Module Based on Wafer-Scale Micromachined Palladium-Silver Alloy Membranes", The 12th International Conference on Solid State Sensors, Actuators and Microsystems, Boston, Jun. 8-12 (2003).

Walter et al., "Sensors from electrodeposited metal nanowires", Surface and Interface Analysis, vol. 34, pp. 40-412 (2002).

Yun et al., "Nanowire Growth for Sensor Arrays", Nanfabrication Technologies, Ed. E.A. Dobisz. SPIE Proceedings 5220, pp. 1-9 (2003).

PCT Search Report for related application PCT/US03/27083, mailed May 27, 2004.

PCT Search Report for related application PCT/US04/17324, mailed Sep. 19, 2005.

* cited by examiner

*Primary Examiner* — Randy Boyer
(74) *Attorney, Agent, or Firm* — Kelly Kordzik; Matheson Keys & Kordzik PLLC (57) ABSTRACT

The present invention is directed to methods and systems of modulating step function phenomena by varying nanoparticle size—particularly wherein a plurality of such nanoparticles are employed, and wherein said nanoparticles comprise a size distribution favorable for collectively smoothing the step function. Such methods and systems are particularly favorable for hydrogen sensors.

3 Claims, 11 Drawing Sheets

Pd    NO HYDROGEN

Fig. 6A

HYDROGEN PRESENT

MODULATION OF STEP FUNCTION PHENOMENA BY VARYING NANOPARTICLE SIZE

This application for patent claims priority to U.S. Provisional Patent Application Ser. No. 60/791,130, which is hereby incorporated by reference herein.

FIELD OF THE INVENTION

The present invention relates generally to nanoscale materials, and specifically to methods and systems of modulating step function phenomena (e.g., phase changes) by varying nanoparticle size—particularly wherein a plurality of such nanoparticles are employed, and wherein such nanoparticles comprise a size distribution favorable for collectively smoothing the step function.

BACKGROUND

Step function phenomena are widespread in nature. Examples of such phenomena are crystalline phase changes and changes in state (e.g., solid to liquid). For homogeneous materials, such changes are generally discrete.

As a particular example of how such changes can be utilized in applications, a palladium nanowire hydrogen sensor has been described which operates with a response that is inverse to that typically seen in palladium-based hydrogen sensors, i.e., it realizes a decreased resistance when exposed to hydrogen (F. Favier, E. C. Walter, M. P. Zach, T. Benter, R. M. Penner "Hydrogen Sensors and Switches from Electrodeposited Palladium Mesowire Arrays," *Science*, 293, p. 2227-2231, 2001). Such nanowires are electrodeposited from perchloric acid ($HClO_4$) solutions onto an electrically-biased graphite step ledge (presumably, these terraced step ledges produce an enhanced field leading to selective deposition). Once formed, these nanowires are transferred to an insulating glass substrate using a cyanoacrylate film. The diameters of these wires are reportedly as small as 55 nm, and they possess gaps or break-junctions which impart them with high resistance. When hydrogen is introduced, a palladium-hydride ($PdH_x$) forms. At room temperature (25° C.), there is a crystalline phase change from α to β when the concentration of hydrogen in air reaches 2% (15.2 Torr). Associated with this phase change is a corresponding 3.5% increase in the lattice parameter of the metal which leads to a "swelling" of the nanowire, thus bridging the nanogap breakjunctions (nano-breakjunctions) and leading to an overall decrease in the resistance along the length of the nanowire. The resistance change that occurs is between 6 and 8 orders of magnitude (typical devices see $1\times10^{-11}$ amps in the "off" state, and $1\times10^{-4}$ amps in the "on" state). This behavior is unique to nanowires possessing such nanogap breakjunctions. Fortunately, for sensor applications, these gaps re-open when the nanowires are removed from the hydrogen-containing environment, and the swollen nanowires revert back to their pre-swollen state.

Such above-described sensors have a number of limitations pertaining both to their use and a methods by which they are made. Perhaps most limiting, is their ability to serve merely as a "on/off" sensor by virtue of their crystalline phase change upon exposure to a threshold hydrogen concentration.

As a result of the foregoing, a method for modulating or smoothing step function phenomena would be quite beneficial, particularly where such smoothing permits such above-described hydrogen sensors to be used as continuous-range sensors.

BRIEF DESCRIPTION OF THE INVENTION

The present invention is directed to methods and systems of modulating step function phenomena by varying nanoparticle size—particularly wherein a plurality of such nanoparticles are employed, and wherein such nanoparticles comprise a size distribution favorable for collectively smoothing the step function.

In some embodiments, the present invention is directed to a method comprising the steps of: (a) providing a plurality of nanoparticles comprising a range of diameters; and (b) using the nanoparticles collectively to smooth step function phenomena. In such methods, the smoothing of step function phenomena is a function of the range of nanoparticle sizes.

In some embodiments, the present invention is directed to a hydrogen sensor comprising a plurality of nanoparticles on a substrate in the form of at least one discontinuous film and spanning source and drain electrodes, wherein the nanoparticles undergo a crystalline phase change and expand upon exposure to a threshold concentration of hydrogen, thereby completing a circuit between the source and drain electrodes, wherein the nanoparticles are present in a range of diameters such that nanoparticles of different diameters undergo the crystalline phase change at different threshold concentrations of hydrogen, and wherein the sensor provides continuous sensing over a range of hydrogen concentrations by virtue of the range of nanoparticle diameters.

In some embodiments, the present invention is directed to a method for sensing hydrogen, the method comprising the steps of: (a) providing a plurality of metal nanoparticles on a substrate in the form of at least one discontinuous film spanning source and drain electrodes, wherein the nanoparticles are present in a range of diameters; and (b) exposing the nanoparticles to hydrogen such that the nanoparticles undergo a crystalline phase change and expand upon exposure to a threshold concentration of hydrogen, thereby completing a circuit between the source and drain electrodes, wherein nanoparticles of different diameters undergo the crystalline phase change at different threshold concentrations of hydrogen, thereby providing sensing over a range of hydrogen concentrations.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIGS. 1(*a*)-1(*f*) depict sensor response progression as Pd radius $r_0$ is increased through radii (a) 2, (b) 5, (c) 15, (d) 22, (e) 30, and (f) 40 nm, wherein the calculated responses are based on bulk Pd measurements;

FIGS. 6(*a*)-6(*d*) illustrate a Pd lattice with (a) no hydrogen present, (b) hydrogen present, (c) low H/Pd loading ratio, and (d) high H/Pd loading ratio;

DETAILED DESCRIPTION OF THE INVENTION

The present invention is generally directed to methods and systems of modulating step function phenomena by varying nanoparticle size—particularly wherein a plurality of such nanoparticles are employed, and wherein such nanoparticles comprise a size distribution favorable for collectively smoothing the step function. While decreasing the size of a material from the bulk to the nanoscale changes or alters the conditions at which a step function occurs, embodiments of the present invention rely on a plurality of nanoparticles having a range of sizes to smooth the step function. Accordingly, by tailoring the size distribution of a plurality of nanoparticles, step function phenomena can be smoothed relative to what is typically observed in the bulk.

"Step function phenomena," as defined herein, are physical changes that occur in discrete steps. Such phenomena include crystalline phase changes. An exemplary such crystalline phase change involves the introduction of hydrogen into a palladium (Pd) lattice. When hydrogen is introduced, a palladium-hydride ($PdH_x$) forms. At room temperature (25° C.), there is a crystalline phase change from α to β when the concentration of hydrogen in air reaches 2% (15.2 Torr). Associated with this phase change is a corresponding 3.5% increase in the lattice parameter of the bulk metal.

"Nanoparticles," as defined herein, are generally particles with diameters in the range of from about 1 nm to about 500 nm. When deposited on a substrate, particularly in the form of a discontinuous film, such nanoparticles may also be referred to as "nano-bumps" and/or "nano-islands." Such nanoparticles may also be quantum confined, wherein they are referred to as "quantum dots." Those of skill in the art will recognize that such nanoparticles can be irregularly-shaped and not necessarily spherical.

In some embodiments, the present invention is directed to a hydrogen sensor comprising a plurality of nanoparticles on a substrate in the form of at least one discontinuous film and spanning source and drain electrodes, wherein the nanoparticles undergo a crystalline phase change and expand upon exposure to a threshold concentration of hydrogen, thereby completing a circuit between the source and drain electrodes, wherein the nanoparticles are present in a range of diameters such that nanoparticles of different diameters undergo the crystalline phase change at different threshold concentrations of hydrogen, and wherein the sensor provides continuous sensing over a range of hydrogen concentrations by virtue of the range of nanoparticle diameters.

In the above-described embodiments, the discontinuous film of nanoparticles can be electrodeposited onto a substrate. In some embodiments, the sensor comprises a single array of nanoparticles having a range of diameters. In some or other embodiments, the sensor comprises multiple arrays of nanoparticles having substantially homogeneous diameters with a particular array, but the nanoparticle diameters varying from array to array.

In some embodiments, the present invention is directed to a method for sensing hydrogen, the method comprising the steps of: (a) providing a plurality of metal nanoparticles on a substrate in the form of at least one discontinuous film spanning source and drain electrodes, wherein the nanoparticles are present in a range of diameters; and (b) exposing the nanoparticles to hydrogen such that the nanoparticles undergo a crystalline phase change and expand upon exposure to a threshold concentration of hydrogen, thereby completing a circuit between the source and drain electrodes, wherein nanoparticles of different diameters undergo the crystalline phase change at different threshold concentrations of hydrogen, thereby providing sensing over a range of hydrogen concentrations.

In some of the above-described embodiments, the nanoparticles comprise metal. In some embodiments, the metal is an alloy. In some embodiments, the metal comprises palladium. In some such embodiments, the palladium may be alloyed with silver (Ag) or another suitable metal.

In some of the above-described embodiments, the sensor/sensing may be based on a drop in resistance across the sensing element, when such element is exposed to hydrogen. The key, however, is that the sensors/sensing provided by the present invention provides sensing over a continuous range of hydrogen concentrations by effectively smoothing the step function response. Those of skill in the art will recognize that such sensors/sensing could also be followed by monitoring a property such as conductance, and that regardless of the physical property so monitored, the sensor must be calibrated with known concentrations.

The following examples are provided to more fully illustrate some of the embodiments of the present invention. It should be appreciated by those of skill in the art that the techniques disclosed in the examples which follow represent techniques discovered by the inventors to function well in the practice of the invention, and thus can be considered to constituted exemplary modes for its practice. However, those of skill in the art should, in light of the present disclosure, appreciate that many changes can be made in the specific embodiments that are disclosed and still obtain a like or similar result without departing from the spirit and scope of the invention.

Example 1

While not intending to be bound by theory, this Example illustrates the Inventor's current understanding of the nanoparticle-based smoothing of step function phenomena—as seen in the above-described hydrogen sensor—as a result of modeling data.

For a hydrogen sensor comprising Pd nanoparticles on a titanium (Ti) substrate, a simple contacting Pd sphere model was examined as a function of Pd radius $r_0$ for 3 initial internuclear sphere separations: 1.994 $r_0$, 2.0 $r_0$ and 2.006 $r_0$. FIGS. 1(*a*)-1(*f*) show the sensor response progression as $r_0$ is increased through radii 2, 5, 15, 22, 30 and 40 nm. The limiting sensor response for high hydrogen pressure increases with larger Pd sphere radii. This is simply a manifestation of an effectively thicker Pd film when the Pd spheres are larger, which results in a larger volume of Pd participating in lowering the Pd resistance. The sensor response could also be increased (meaning a larger resistance change) by making the Pd channel wider but keeping the Ti channel the same width.

Figure 1A:
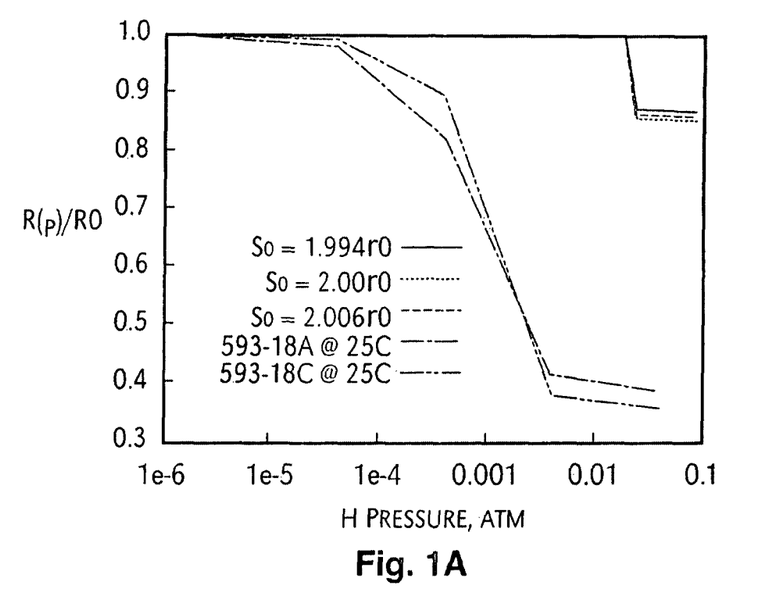
Figure 1B:
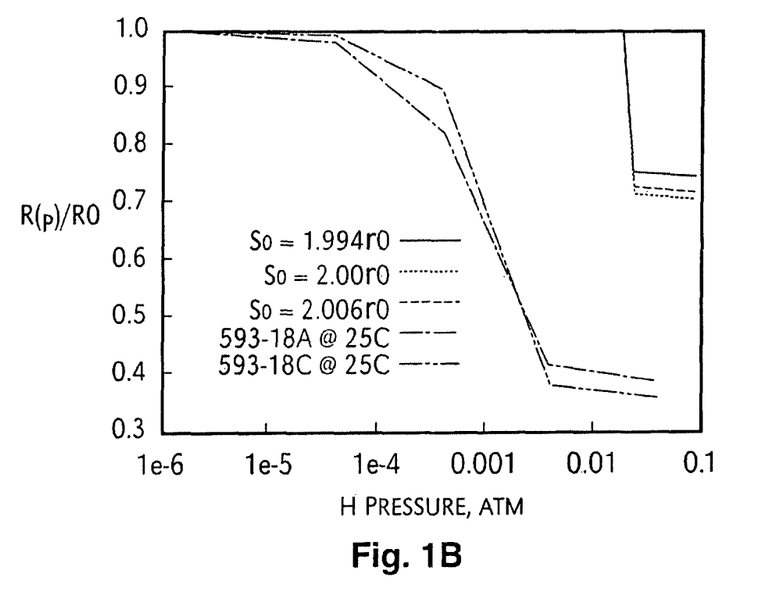
Figure 1C:
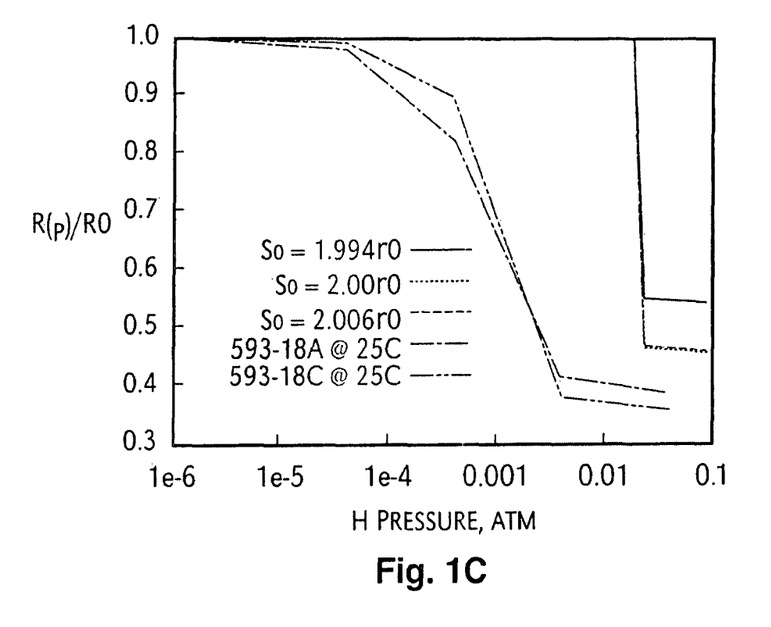
Figure 1D:
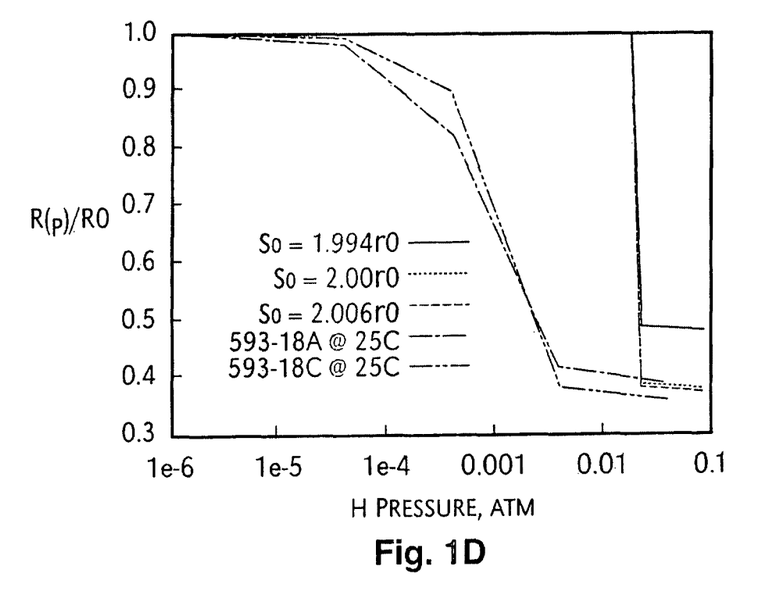
Figure 1E:
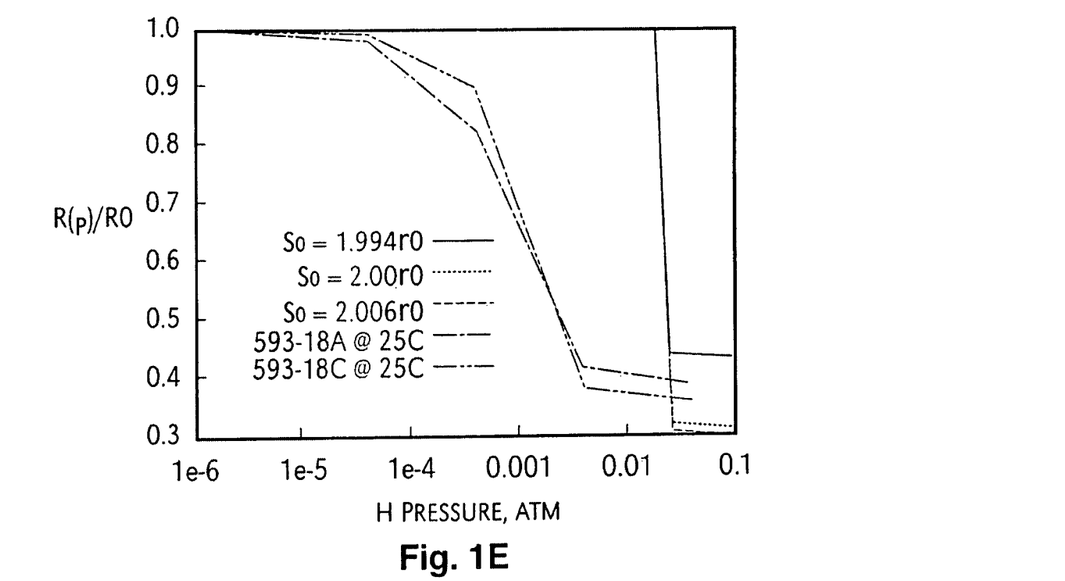
Figure 1F:
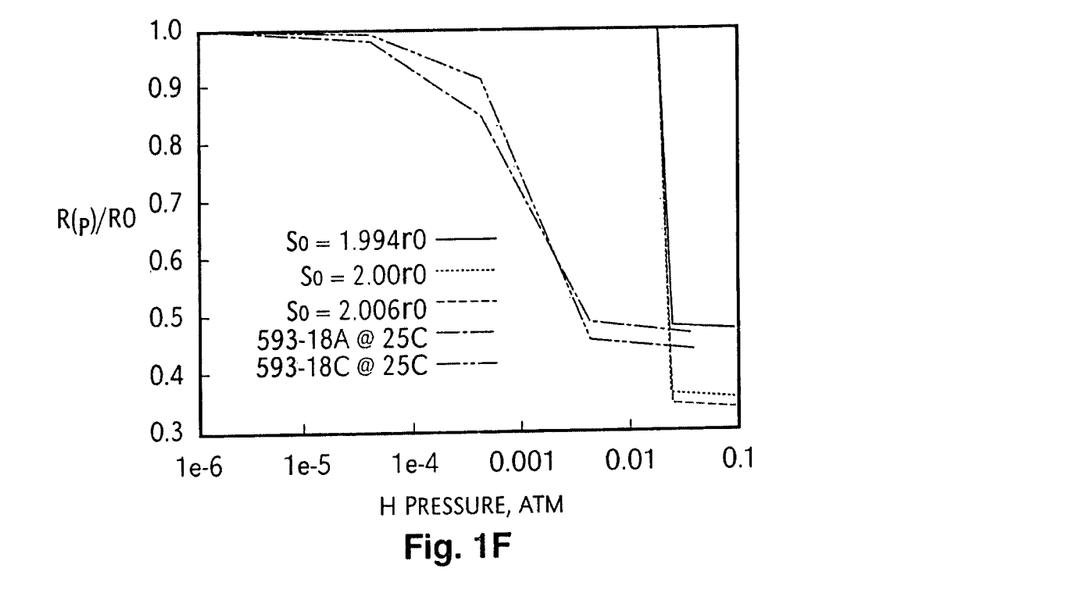
Figure 2:
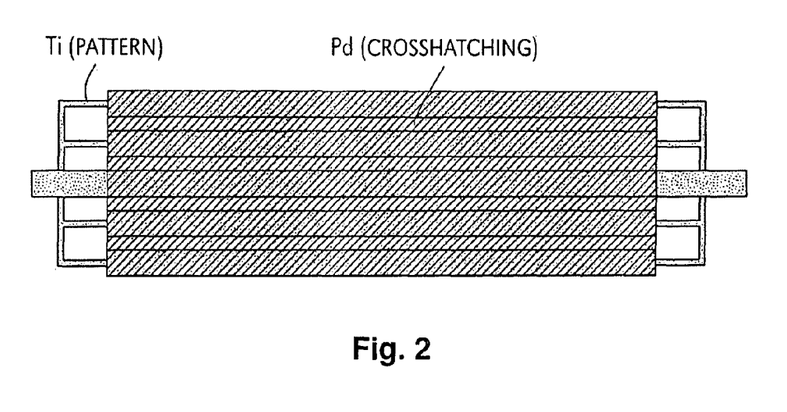
FIG. 2 illustrates how a Ti substrate could be patterned with sacrificial interconnects that would allow electrolysis growth of Pd, in accordance with some embodiments of the present invention.

It may be possible to create a sensor with a Pd area greater than the underlying Ti area. The Ti could be patterned with sacrificial interconnects that would allow electrolysis growth of the Pd (FIG. 2). The interconnect traces would then be cut to reduce the underlying Ti resistance that would be measured as the initial sensor resistance $R_0$. Now that this does not have to assume the Pd is electrically insulated from the Ti layer. If the Pd is insulated from the Ti, the sensor clearly has a larger response. If the Pd was electrically connected to the Ti layer, then as each channel makes contact with its neighbor via the Pd, the parallel resistance of the Ti channel would further help to increase the total sensor response. In any case, measurements of this scheme could indicate whether the Pd is indeed insulated from or contacted to the Ti.

Extrapolating the Pd Expansion

A functional form for the H/Pd ration (hydrogen loading fraction f) as a function of pressure can be contrived so that the modeled sensor response matches the measured sensor response. A desired shape for the curve can be modeled by one minus a Fermi functional form, e.g., $$f = 1 - \frac{1}{2 \times 10^3 e^{3\log_{10}(p)} + 1}$$

where p is the hydrogen pressure.

Figure 3:
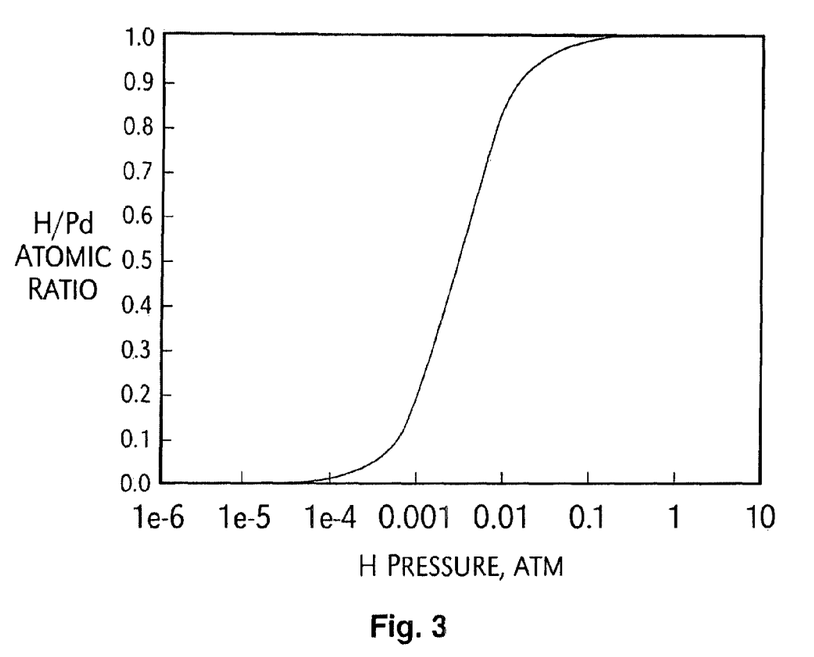
FIG. 3 is a modeled plot of H/Pd atomic ratio to H pressure, for a range of Pd nanoparticle sizes.

The constants were chosen by eyeballing the fit to the measured data, with the factor in front of the exponential function adjusting the "width" of the ramp up and the factor multiplying the $\log_{10}$ function adjusting the minimum ratio value at the left side of the graph. Comparing the postulated H/Pd ratio (FIG. 3) to the measured bulk Pd ratio (FIG. 4) shows the hydrogen being absorbed into the Pd at lower pressures than the bulk measurements indicate, and the smoother behavior resulting in a smoother modeled response—which is what is required in this simple model to mimic the measured response. Physically, this indicates the palladium acts as a better sponge for the hydrogen when the Pd has a greater surface-to-volume ratio, i.e., for for smaller Pd particles.

The effective lattice constant again is considered as a linear fit between the α-phase lattice constant at a H/Pd ratio of zero to the greater β-phase lattice constant at unity H/Pd ratio. Thus, the plot of the H/Pd ratio in FIG. 3 can also be considered a plot of lattice constant vs. H pressure, where now the ordinate scale runs from 0.3892 nm at the bottom to 0.4026 nm at the top of the graph.

Figure 5:
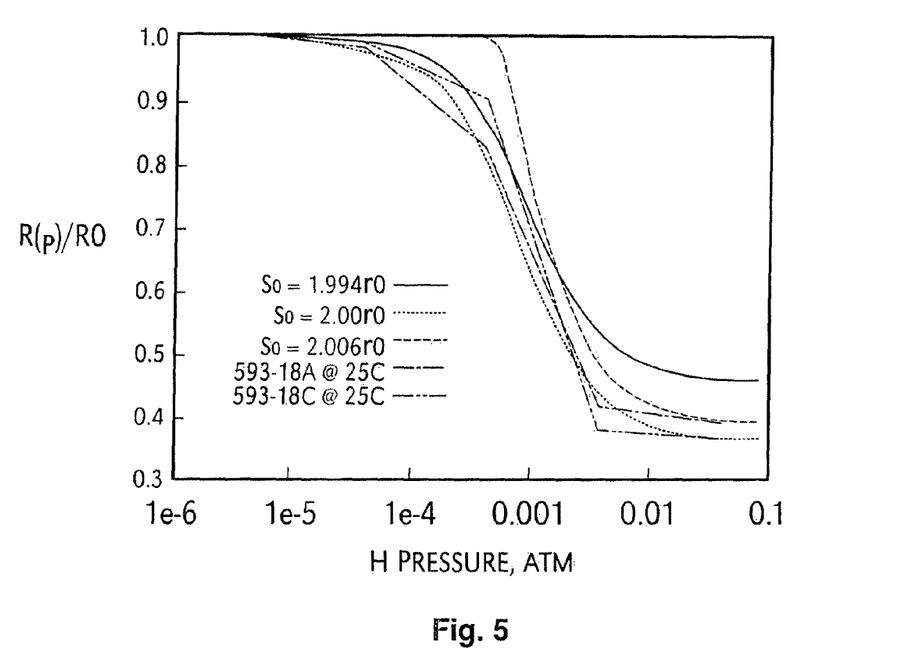
FIG. 5 depicts the modeled sensor response for Pd nanoparticles.

FIG. 5 shows the modeled sensor response for Pd particles of diameter 30 nm and for three initial particle separations: initially non-contacting, just at the verge of contacting, and already contacting. The measured response of actual sensors 593—18A and 18C (hydrogen sensors of the present invention employing nanoparticles of varying diameter) are also shown on the graph. The agreement is quite good.

The Physics

Figure 6A:
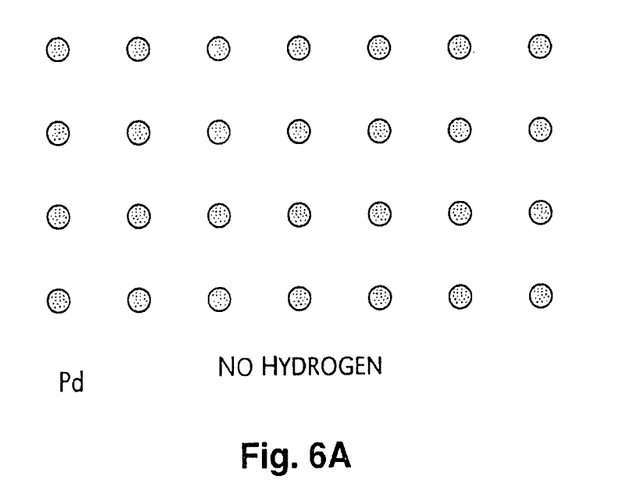
Figure 6B:
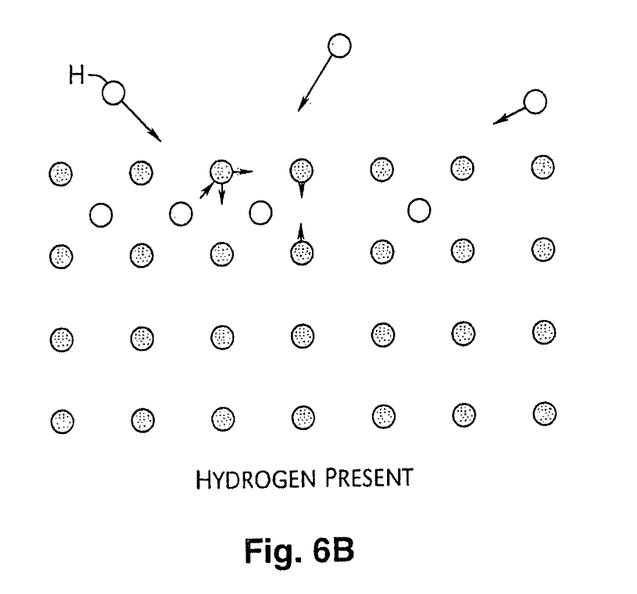

The face centered cubic crystalline Pd lattice interatomic bonding maintains the α phase lattice constant 0.3892 nm as shown in FIG. 6(a). When energetic H atoms impinge on the Pd surface they can force themselves into the Pd lattice structure, but at the cost of energy to separate the local Pd lattice to the β phase lattice constant 0.4026 (FIG. 6(b)). The forces can be viewed as the Pd atoms having attractive interatomic forces working against the repelling force of the embedded hydrogen atom.

The palladium lattice wants to expel the hydrogen atoms (it is energetically favorable), which is clear since the H depletes in the absence of a hydrogen atmosphere. The hydrogen atmosphere constantly bombards the Pd surface, with the surface H molecules and atoms "pushing" against the H atoms just beneath the surface to create a hydrogen current, i.e., a flux directed to the inside of the Pd. If one imagines a single H atom deep inside bulk palladium it executes a random walk until it reaches an external surface and is expelled. That is the diffusion process, but now with an external flux of H atoms or molecules a net hydrogen flow is created until the H/Pd ratio reaches equilibrium for the given H gas pressure (surface flux).

Figure 6C:
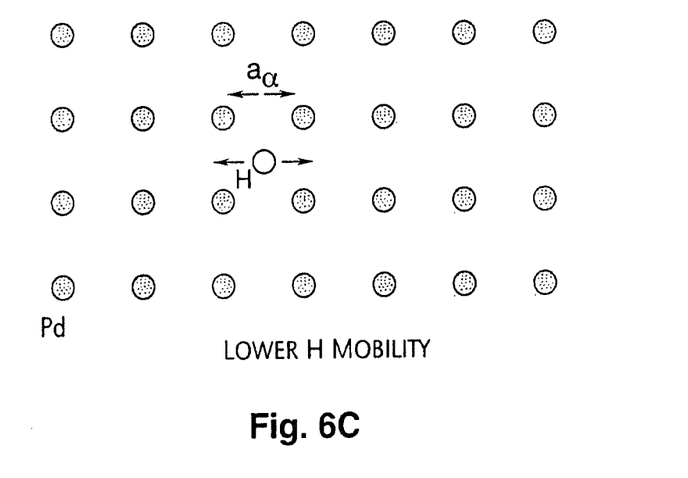
Figure 6D:
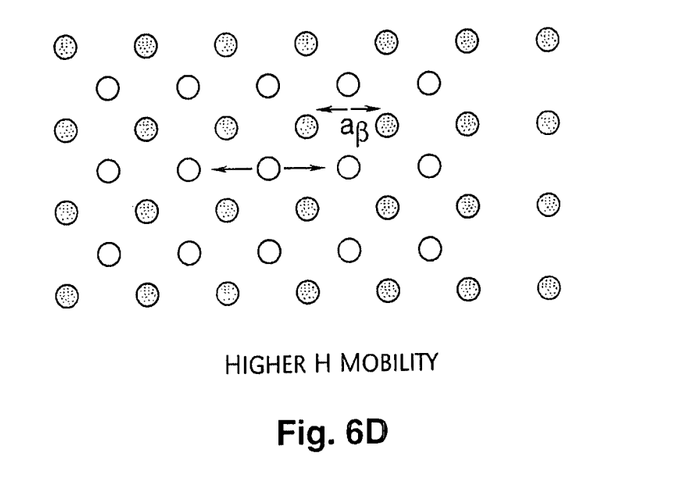

With this model of hydrogen penetration and movement inside the Pd lattice it is predicted that at low H/Pd loading ratios the hydrogen mobility and diffusion constant are lower because the H atom is always being forced to separate two Pd atoms further apart (FIG. 6(c)). When the H/Pd ratio is larger, the Pd atoms are already mostly separated by the larger, β-phase lattice constant, so an H atom has less of a potential barrier to move to a new lattice site (FIG. 6(d)).

Figure 7:
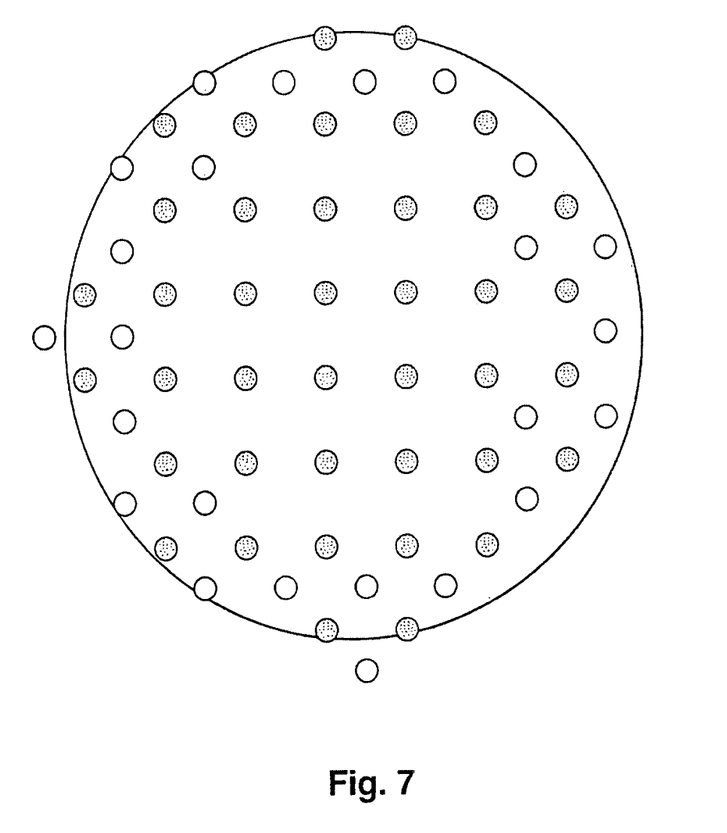
FIG. 7 illustrates the surface to bulk ratio of Pd atoms in a nanoparticle.

This model would also predict that surface absorption is easier because the external surface Pd atoms have less interatomic forces holding them in position because there are fewer Pd atom neighbors (FIG. 7). That is qualitatively consistent with the Pd nanoparticle hydrogen sensor being sensitive at a H pressure range well below what bulk H—Pd measurements would predict. The model also explains the hysteresis observed between the H/Pd ratio-pressure-curves for increasing H pressure versus the curve for decreasing H pressure. Once H atoms near the surface are expelled from the palladium, the Pd atoms try to relax back to the shorter α-phase lattice constant. This simultaneously makes the H atoms have less mobility near the palladium surface, effectively trapping them inside, and also introduces stresses at the H loaded-H non-loaded boundaries. The stresses are the origin of hydrogen embrittlement in metals.

Example 2

This Example serves to illustrate a method of constructing a continuous range sensing device where the underlying sensitivity is a step function by using a plurality of step function elements with tailored step points, in accordance with some embodiments of the present invention.

Figure 8:
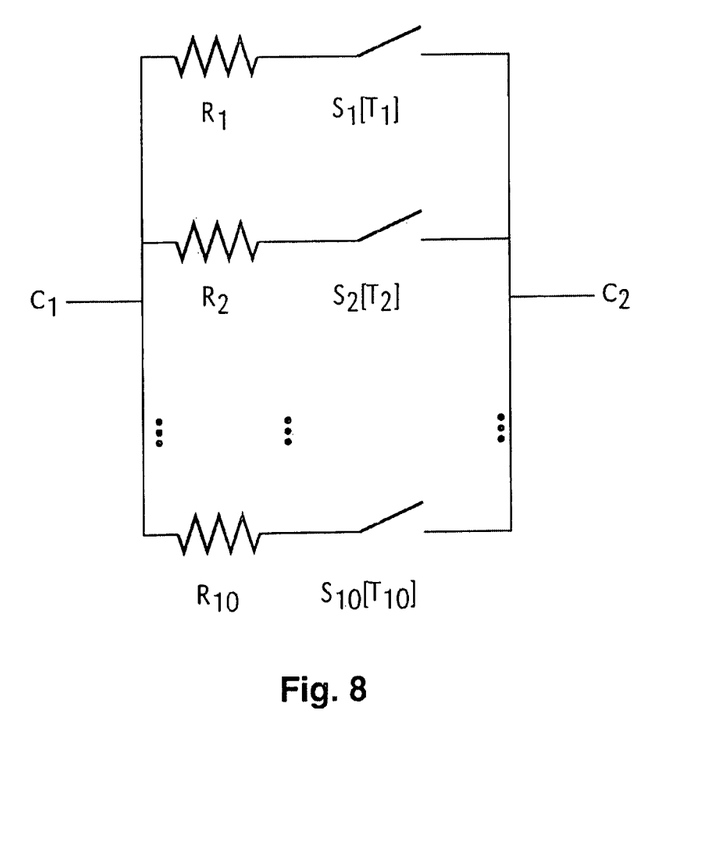
FIG. 8 illustrates (as a household thermostat) a sensor-type device with a plurality of sensing elements having different response points, wherein such sensing elements are arranged in parallel, in accordance with some embodiments of the present invention.

Here, a device is described possessing a response that varies continuously according to a continuously variable stimulus, with the device being constructed as a composite of multiple fundamental elements each of which possesses only a step function response to the stimulus. An illustrating example is a household thermostat, which produces a step function response by the closing of a switch; the thermostat state is either "on" or "off." But when one has 10 such thermostats in their possession, each individual response point, e.g., the temperature where the switch closes, can be tailored by adjusting the temperature setting. Now if each thermostat/switch was, for example, placed in series with a resistor, and the 10 resistor-switch pairs placed in parallel the resistance of the complete device can be used to measure the temperature, with the resolution and sensitivity range being a function of the number of resistor-switch pairs, FIG. 8.

Figure 4:
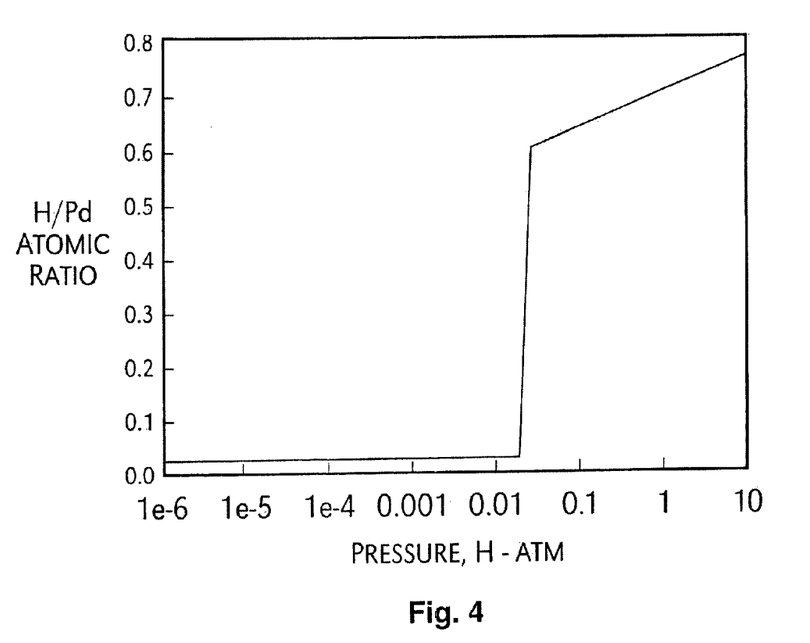
FIG. 4 is a plot of H/Pd atomic ratio to H pressure for bulk Pd.

A specific practical embodiment of the claim relates to the step function like hydrogen loading in a palladium lattice as a function of the hydrogen pressure, FIG. 4. The low line to the left of the step is the α-phase of the palladium lattice possessing a lattice constant of 0.3892 nm, while the upper line to the right of the step is the β-phase having a lattice constant of 0.4026 nm. There is little to no width to the region encompassing the step so trying to measure hydrogen pressure as a function of the hydrogen loading essentially provides only an above or below 0.02 atmosphere on-off reading. If the hydrogen loading step can be moved from 0.02 atmospheres, i.e., tailored to be at a different location on the abscissa, then a device can be constructed analogous to the preceding thermostat switch plus resistor illustration. That would allow a composite device to have a continuous response (like a resistivity or an expansion coefficient) as a function of the stimulus (the hydrogen pressure).

A specific method to vary where the step in FIG. 4 is located can be by varying a nanosize particle of palladium's diameter, where the hydrogen loading fraction is believed to depend on lattice strain which will vary for a given number of hydrogen atoms in relation to the total number of palladium atoms in the particle. Ten hydrogen atoms lost in bulk palladium is a completely different regime than ten hydrogen atoms immersed in a 100 palladium atom particle.

In conclusion, the present invention provides to methods and systems of modulating step function phenomena by varying nanoparticle size—particularly wherein a plurality of such nanoparticles are employed, and wherein such nanoparticles comprise a size distribution favorable for collectively smoothing the step function. Such methods and systems are particularly favorable for the Pd-based hydrogen sensors described above.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

The invention claimed is:

1. A hydrogen sensor comprising a plurality of nanoparticles on a substrate in the form of at least one discontinuous film and spanning source and drain electrodes,
   wherein the nanoparticles are configured to undergo a crystalline phase change and expand upon exposure to a threshold concentration of hydrogen, thereby completing a circuit between the source and drain electrodes,
   wherein the nanoparticles are present in a range of diameters such that nanoparticles of different diameters are configured to undergo the crystalline phase change at different threshold concentrations of hydrogen, and
   wherein the sensor is configured to provide continuous sensing over a range of hydrogen concentrations from $10^{-5}$ atm to $10^{-2}$ atm in air at atmospheric pressure by virtue of the range of nanoparticle diameters.

2. The hydrogen sensor of claim 1, wherein the nanoparticles are metal.

3. The hydrogen sensor of claim 2, wherein the nanoparticles comprise palladium.

* * * * *